United States Patent [19]

Ali

[11] 4,420,517

[45] Dec. 13, 1983

[54] METHODS FOR IMPROVING UNIFORMITY OF SILICA FILMS ON SUBSTRATES

[75] Inventor: Keramat Ali, Sumter, S.C.

[73] Assignee: Becton Dickinson and Company, Paramus, N.J.

[21] Appl. No.: 375,635

[22] Filed: May 6, 1982

[51] Int. Cl.³ .......................... A01N 1/02; B05D 3/02; B32B 9/04
[52] U.S. Cl. .......................................... 428/35; 427/2; 427/397.7; 428/446; 604/403; 604/408
[58] Field of Search ................ 427/2, 397.7; 428/446, 428/35; 604/403, 408, 415, 416

[56] References Cited

U.S. PATENT DOCUMENTS

| | | | |
|---|---|---|---|
| 2,855,329 | 10/1958 | Morton | 427/397.7 |
| 4,069,185 | 1/1978 | Sullivan | 260/29.6 HN |
| 4,112,925 | 9/1978 | Sullivan | 128/2 F |
| 4,153,739 | 5/1979 | Kessler | 427/2 |
| 4,257,886 | 3/1981 | Kessler | 210/516 |

OTHER PUBLICATIONS

*Properties and Applications of Oxide Layers Deposited on Glass from Organic Solutions*, H. Schroeder, Oct. 20, 1961.
*Ultrapure $SiO_2$ and $Al_2O_3$ for the preparation of Low Loss Compound Glasses*, Gossink, R. G. et al., Mat. Res. Bull., vol. 10, pp. 35-40, 1975.
*Monolithic Glass Formation by Chemical Polymerization*, Yolbas, B. E., Journal of Materials Science, vol. 14, 1979.
*Preparation of a gel from Metal Alkoxide and Its Properties as a Precursor of Oxide Glass*, Yamanc, Masayuki; Journal of Materials Science, vol. 13, 1978.
*Preparation of Glasses and Ceramics from Metal-Organic Compounds*, Yoldas, B. E., Journal of Materials Science, vol. 12, 1977.
Silicon Compounds, Register and Review, a catalog of Petrarch Systems, Inc.
Low-Heat Glass Aims for High Technology, Chemical Week, p. 65, Jun. 18, 1980.

*Primary Examiner*—Michael R. Lusignan

[57] ABSTRACT

A process is provided for enhancing the uniformity of silica coatings on substrates, such as evacuated blood collection tubes for example, which increased uniformity results in a substantial increase in the active surface area of the silica for improved clot activation. The process includes hydrolyzing a mixture of ethylsilicate and isopropyl alcohol in the presence of an acid or alkaline solution to precipitate out the silica. The silica sol which results is applied to the substrate, and dried in the presence of low heat application. Alternatively, the silica sol may be mixed with a water soluble carrier such as polyvinyl pyrrolidone, if desired, prior to application to the substrate, if the silica is to be released into a water based substance, such as blood, for example subsequently introduced into the coated container.

16 Claims, 1 Drawing Figure

METHODS FOR IMPROVING UNIFORMITY OF SILICA FILMS ON SUBSTRATES

BACKGROUND OF THE INVENTION

This invention relates to methods for coating a substrate with a film of silica. More particularly, this invention relates to such a process which increases the uniformity of the film on the substrate which property of uniformity has the effect of increasing substantially the active surface area of the silica. More particularly, this invention relates to such a process for use in, for example, coating blood sample collection tubes such as serum separation tubes to increase the clot activation properties thereof once a blood sample is introduced into the tube.

The length of time required for blood collected in a blood collection assembly to clot after it is introduced into the assembly is dependent upon a number of interrelated factors. One of the factors which increases the rate of clot formation is exposure of the blood to "siliceous" materials such as glass, silica, kaolin, bentonite or diatomaceous earth. Therefore, it is important that the exposure of the blood sample to the presence of a silica in a sample containing tube be as uniform and rapid as possible.

Representative prior art patents which teach among other things, silica coatings in blood collection tubes, such as serum separation tubes, include U.S. Pat. Nos. 4,153,739 and 4,257,886. The '739 patent teaches a clot activating film 24 with the film being formed of 1% by weight polyvinyl pyrrolidone and 1% by weight silica added to isopropanol. In substitution for polyvinyl pyrrolidone, polyethylene oxide may be used. The '886 patent teaches, on the other hand, a water-soluble clot activating coating 36 wherein the coating is comprised of an admixture of polyvinyl pyrrolidone or polyethylene oxide with clot activating particles such as silica in a solvent such as isopropanol. In both cases, the source of the silica is fine silica particles.

While the methods taught in the two patents have proved satisfactory in the sense that they produce coatings on substrates such as serum separation tubes which coatings contain silica for clot activation, the films have not proved entirely satisfactory in the sense that they are not as uniform as desired. Because of this, there is less surface active area for bringing about the desired clot activation. It has been found that one way to overcome this problem in order to achieve the best coatings, it is necessary to include Freon in combination with the isopropyl alcohol in order to secure a proper uniform coating. Freon also lowers the flash point of isopropyl alcohol during the drying cycle. However, Freon is expensive and creates corrosion problems in processing equipment for obtaining the coatings.

DESCRIPTION OF THE INVENTION

With this invention, by contrast, an extremely uniform silica coating is provided. The silica is obtained in the form of colloidal silica obtained by the hydrolysis of ethylsilicate which forms a sol, which sol results in a uniform coating after application and drying. If desired, the sol, prior to being coated onto the substrate, may have added to it polyvinyl pyrrolidone or other water soluble carrier so that the silica particles are coated for a subsequent release, once a water containing sample is introduced against the coating, such as blood for example. Once the blood or other water containing sample is introduced, the carrier such as polyvinyl pyrrolidone will dissolve carrying the silica particles with it into solution for carrying out blood clot activation.

In considering generally the conditions for carrying out the process of this invention, ethylsilicate is the source of activated silica in liquid form. The ethylsilicate is hydrolyzed either in a basic or acid media to orthosilicic acid, with the resulting sol, upon standing or heating to a moderate temperature producing silica, according to the formula;

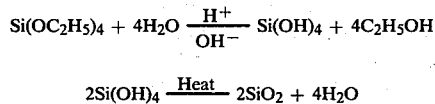

$$2Si(OH)_4 \xrightarrow{Heat} 2SiO_2 + 4H_2O$$

The hydrolysis may be carried out in the presence of ammonia as an alkaline catalyst, or in the presence of hydrochloric acid, acetic acid, or sulfuric acid as an acid catalyst.

As discussed above, if a uniform coating which will adhere to a substrate such as a glass substrate is required, the resulting sol obtained from the hydrolysis procedure as discussed above, is applied to the substrate and dried at a moderately elevated temperature. If, on the other hand, it is desired to have the coating with a property of water solubility, then the sol may be mixed with a water soluble component such as polyvinyl pyrrolidone (PVP) or other water soluble materials, such as methyl cellulose or carboxymethyl cellulose.

In those applications where the silica coating is to be used in a non-water soluble state, the coatings have been found to be particularly useful in the electronic industry for providing silica glass coatings, which, as the result of the process of this invention provide highly uniform coatings, but with an increased surface active area.

With the foregoing and additional objects in view, this invention will now be described in more detail, and other objects and advantages thereof will become apparent from the following description, the accompanying drawing and the appended claims.

DESCRIPTION OF THE FIGURE

The FIGURE is a longitudinal sectional view of a serum separation tube assembly illustrating the invention.

DETAILED DESCRIPTION OF THE INVENTION

Figure 1:
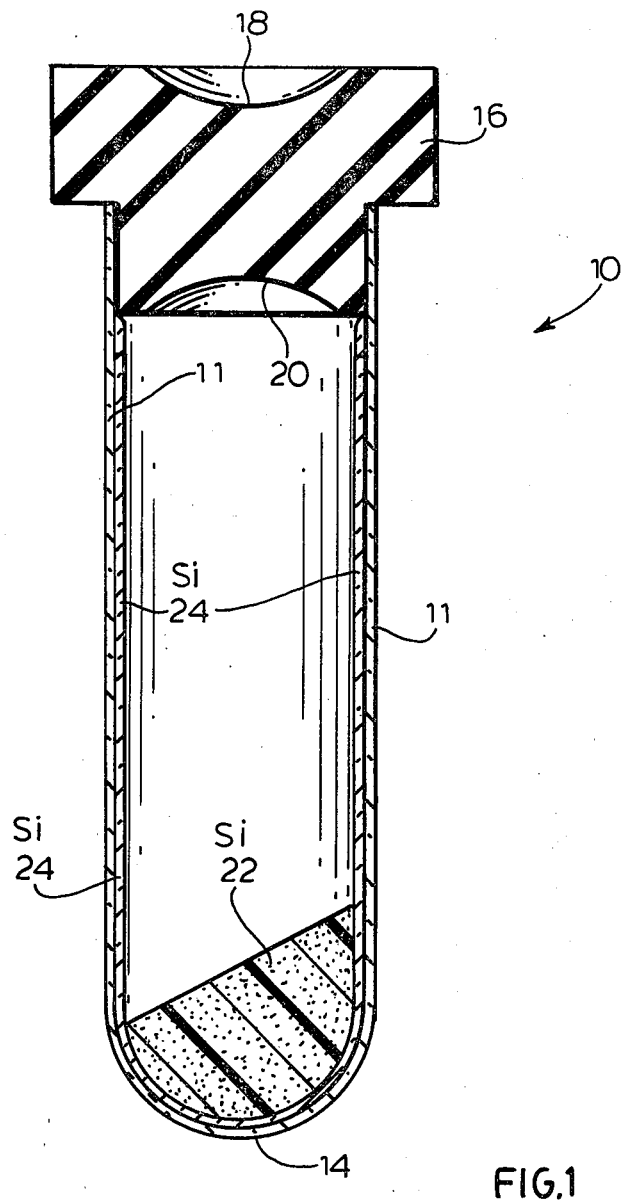

Referring to the FIGURE, a serum separation tube assembly is designated generally 10 having a tube 11, preferably of glass, having a closed end 14 and an open end 12. An elastomeric stopper 16 is disposed in the open end 12 for maintaining an evacuated tube assembly for receiving a blood sample, for example. The elastomeric stopper 16 includes an upper and a lower well 18, 20, respectively, for easing the passage of a cannula therethrough for the introduction of a blood sample into tube 11.

In accordance with this invention, a silica containing coating 24 is applied to the internal surface of tube 11 for the purpose of enhancing clot activation of a blood sample introduced into the tube. Once the coating 24 has been introduced and dried in accordance with the process of the invention herein, a silicon based gel material 22 such as that described in U.S. Pat. No. 3,920,549 may then be positioned in the bottom of tube 11 as shown in the FIGURE. As will be understood by practitioners in the art, the gel material 22 is a thixotropic material which, under the action of centrifugal force, moves upwardly in tube 11 to divide the heavier and lighter fractions of an introduced blood sample.

In considering, generally, the conditions for carrying out the invention, the percent of silica in the final coating solution will be within the range of between about 0.75 and 1.50%. This is achieved, for example, by admixing ethylsilicate and isopropyl alcohol in the ratio of 1:1 by volume. The resulting admixture is hydrolyzed by the addition of an acid or alkaline catalyst to obtain a sol for the coating on the substrate of interest. Then the coating is heated at an elevated temperature within the range of between about 100° and 120° C. for a period of time within the range of between about 5 and 10 minutes. If a water soluble component is added, it is preferably added at within the range of between about 2 and 5% of the silica sol.

As purely illustrative of the process of the invention herein, a specific example was carried out for imparting a silica containing coating to the internal surface of a serum separation tube. It is to be understood, however, that this example is being presented with the understanding that it has no limiting character on the broad disclosure of the invention as generally set forth herein and as directed to men skilled in the art.

EXAMPLE I

A mixture of ethylsilicate and isopropyl alcohol in the ratio of 1:1 by volume was made. The mixture was hydrolyzed by the addition thereto of a 1–2% solution of ammonia at room temperature. Silica in the form of orthosilicic acid precipitated out of the solution. The resulting silica suspension or sol was diluted with a 5% solution of polyvinyl pyrrolidone in water until the total concentration of silica in the final mixture was about 0.75%. This mixture was used to coat the inner surface of several tubes similar in configuration to tube 11 shown in the drawing above. The tubes were heated at a temperature of 110° C. for 10 minutes to evaporate residual water, isopropyl alcohol and ammonia from the tube. The resulting coating was a fine coating of PVP and silica. Subsequent to the drying procedure, stoppers were introduced into the open top of the several tubes containing the coatings and the tubes were partially air evacuated in the usual procedure for producing blood collection tubes.

Further with respect to the example above, if desired, the tubes may have introduced into them a thixotropic gel material, as described in the aforementioned U.S. Pat. Nos. 4,257,886 and 4,153,739, so as to produce blood serum separation tubes. Other subsequent processing steps, may also be applied, depending upon the ultimate testing applications for which the resulting product is used.

As further illustrative of the results achieved with the process of this invention, one may note the comparative results noted below in Example II between the processing procedures of the prior art, in which a silica coating was applied to the internal surfaces of blood collection tubes using a preparation of one (1) percent by weight silica particles having an average diameter of 1.5 microns in isopropanol mixed thoroughly in a blender, and the silica sol of the invention wherein a mixture of ethylsilicate and isopropanol in the ratio of 1:1 by volume was prepared, followed by hydrolysis of the mixture by the addition of a 1–2 percent solution of ammonia. The resulting mixture contained a 1.0% silica concentration. All of the tubes were dried at a temperature of 110° C. for 5 to 6 minutes.

| Prior Art Tube No. | Silica in mg. | Invention Tube No. | Silica in mg. |
|---|---|---|---|
| 1 | 1.9 | 1 | 4.4 |
| 2 | 1.6 | 2 | 3.5 |
| 3 | 1.9 | 3 | 3.9 |
| 4 | 1.9 | 4 | 3.4 |
| 5 | 2.1 | 5 | 3.6 |
| 6 | 1.6 | 6 | 2.8 |
| 7 | 1.5 | 7 | 4.8 |
| 8 | 1.1 | 8 | 2.5 |
| 9 | 1.3 | 9 | 4.6 |
| 10 | 2.1 | 10 | 3.9 |

As can be seen from Example II, because of the uniformity of coatings produced with this invention, there is a substantial increase in the quantity of silica available in the coating, for clot activation for example.

Accordingly, and as will be apparent from the foregoing, there is provided, in accordance with this invention, a method for producing an improved silica coating on substrates which coating is of greatly increased uniformity which in turn provides a greatly increased reactive surface area for subsequent use. In addition, the process herein increases the ease with which such coatings are produced, and without the need for expensive and/or corrosive materials. Thus, the improved products obtained by the process herein are obtained at reduced cost.

While the methods and compositions herein disclosed form preferred embodiments of this invention, this invention is not limited to those specific methods and compositions, and changes can be made therein without departing from the scope of the invention which is defined in the appended claims.

What is claimed is:

1. A process for producing a uniform blood releasable silica coating on the internal surface of a blood collection container, characterized by the steps of
   (a) forming a mixture by admixing ethylsilicate and isopropyl alcohol;
   (b) adding to the mixture formed from said forming step a hydrolyzing material;
   (c) hydrolyzing said mixture obtained from said forming and adding steps to obtain a sol;
   (d) coating said sol obtained from said hydrolyzing step onto the internal surface of a blood collection container; and
   (e) heating said coating from said coating step at elevated temperatures for the period of time necessary to dry said coating.

2. The process of claim 1, further characterized by
   (a) said forming step being carried out with a mixture of ethylsilicate and isopropyl alcohol in the ratio of 1:1 by volume.

3. The process of claim 1, further characterized by
   (a) the hydrolyzing material for said adding step is an aqueous solution of a member selected from the group consisting of ammonia, acetic acid, sulphuric acid and hydrochloric acid.

4. The process of claim 1, further characterized by
   (a) said hydrolyzing step is carried out by adding a 1–2% solution of ammonia to said mixture from said forming step.

5. The process of claim 1, further characterized by (a) said heating step is carried out at a temperature within the range of between about 100 and 120 degrees centigrade.

6. The process of claim 5, further characterized by
   (a) said heating step is carried out for a period of time within the range of between about 5 minutes and 10 minutes.

7. The process of claim 1, further characterized by the additional step prior to said coating step of
   (a) admixing with said sol obtained from said hydrolyzing step an aqueous solution of a member selected from the group consisting of polyvinyl pyrrolidone, methyl cellulose and carboxymethyl cellulose.

8. The process of claim 7, further characterized by
   (a) admixing with said sol obtained from said hydrolyzing step a 5 percent solution of polyvinyl pyrrolidone in water until the total concentration of silica in the final mixture is about 0.75 percent by volume.

9. A blood collection container with a uniform blood releasable silica film coating the internal surfaces thereof, obtained by the process of
   (a) forming a mixture by admixing ethylsilicate and isopropyl alcohol;
   (b) adding to the mixture formed from said forming step a hydrolyzing material;
   (c) hydrolyzing said mixture obtained from said forming and adding steps to obtain a sol;
   (d) coating said sol obtained from said hydrolyzing step onto said internal surfaces of said blood collection container; and
   (e) heating said coating from said coating step at elevated temperatures for the period of time necessary to dry said coating.

10. The container of claim 9, further characterized by
    (a) said forming step being carried out with a mixture of ethylsilicate and isopropyl alcohol in the ratio of 1:1 by volume.

11. The container of claim 9, further characterized by
    (a) the hydrolyzing material for said adding step is an aqueous solution of a member selected from the group consisting of ammonia, acetic acid, sulphuric acid, and hydrochloric acid.

12. The container of claim 9, further characterized by
    (a) said hydrolyzing step is carried out by adding a 1-2% solution of ammonia to said mixture from said forming step.

13. The container of claim 9, further characterized by
    (a) said heating step is carried out at a temperature within the range of between about 100 and 120 degrees centigrade.

14. The container of claim 13, further characterized by
    (a) said heating step is carried out for a period of time within the range of between about 5 minutes and 10 minutes.

15. The container of claim 9, further characterized by
    (a) admixing with said sol obtained from said hydrolyzing step an aqueous solution of a member selected from the group consisting of polyvinyl pyrrolidone, methyl cellulose and carboxymethyl cellulose.

16. The container of claim 9, further characterized by
    (a) admixing with said sol obtained from said hydrolyzing step a 5 percent solution of polyvinyl pyrrolidone in water until the total concentration of silica in the final mixture is about 0.75 percent by volume.

* * * * *